(12) United States Patent
Yancey et al.

(10) Patent No.: US 12,168,792 B2
(45) Date of Patent: Dec. 17, 2024

(54) ENHANCING PRODUCT STREAMS FROM ETHANOL PRODUCTION

(71) Applicant: D3Max, LLC, Grand Forks, ND (US)

(72) Inventors: Mark Yancey, Grand Forks, ND (US); Dale Monceaux, Lakewood, CO (US); Neal Kemmet, Stanley, WI (US); Joe Fischer, Eau Claire, WI (US); Colton Walz, Elk Mound, WI (US)

(73) Assignee: D3MAX, LLC, Grand Forks, ND (US)

( * ) Notice: Subject to any disclaimer, the term of this patent is extended or adjusted under 35 U.S.C. 154(b) by 0 days.

(21) Appl. No.: 17/804,052

(22) Filed: May 25, 2022

(65) Prior Publication Data

US 2022/0290191 A1 Sep. 15, 2022

Related U.S. Application Data

(63) Continuation of application No. 17/200,053, filed on Mar. 12, 2021.

(60) Provisional application No. 62/989,423, filed on Mar. 13, 2020.

(51) Int. Cl.
*C12P 7/14* (2006.01)
*C07H 1/08* (2006.01)
*C12P 19/02* (2006.01)

(52) U.S. Cl.
CPC .............. *C12P 7/14* (2013.01); *C07H 1/08* (2013.01); *C12P 19/02* (2013.01)

(58) Field of Classification Search
CPC ......... C12P 7/14; C12P 19/02; C12P 2201/00; C12P 7/10; C12P 19/14; C07H 1/08; Y02P 60/87; A23K 10/38; C11B 1/025; C13K 1/02; C13K 13/007
See application file for complete search history.

(56) References Cited

U.S. PATENT DOCUMENTS

| | | | |
|---|---|---|---|
| 4,309,254 A | 1/1982 | Dahlstrom et al. | |
| 5,411,594 A | 5/1995 | Brelsford | |
| 6,444,437 B1 | 9/2002 | Sporleder et al. | |
| 8,288,138 B2 | 10/2012 | Birkmire et al. | |
| 8,633,003 B2 | 1/2014 | Brotherson | |
| 9,193,982 B2 * | 11/2015 | Sjoede | C13K 1/02 |
| 9,434,961 B2 | 9/2016 | Dottori et al. | |
| 10,947,487 B2 | 3/2021 | Godoy | |
| 2009/0093027 A1 | 4/2009 | Balan et al. | |
| 2013/0164804 A1 | 6/2013 | Walther et al. | |
| 2014/0206055 A1 * | 7/2014 | Ramos | C12P 7/14 435/165 |

FOREIGN PATENT DOCUMENTS

EP 0169068 A2 1/1986

OTHER PUBLICATIONS

Zhang et al., Ethanol From Corn Stover Using SSF: An Economic Assessment . Energy Sources, Part B, 2011, vol. 6: 136-144. (Year: 2011).*
Kazi et al., Techno-Economic Analysis of Biochemical Scenarios for Production of Cellulosic Ethanol. Technical Report, NREL/TP-6A2-46588, Jun. 2010, pp. 1-202. (Year: 2010).*
Gregg et al., Factors Affecting Cellulose Hydrolysis and the Potential of Enzyme Recycle to Enhance the Efficiency of an Integrated Wood to Ethanol Process. Biotechnol. Bioeng., 1996, vol. 51: 375-383. (Year: 1996).*
Vallander et al., Enzyme recirculation in saccharification of lignocellulosic materials. Enzyme Microb. Technol., 1987, vol. 9: 714-720. (Year: 1987).*
Willington, et al., Options for Handling Stillage Waste from Sugar-Based Fuel Ethanol Production, Resources and Conservation 8, 1982, 111-129.
Final Office Action dated Apr. 17, 2023 issued in U.S. Appl. No. 17/200,053.
Karimi et al., Conversion of rice straw to sugars by dilute-acid hydrolysis, Biomass Bioenergy, 2006, vol. 30: 247-253 (Year: 2006).
Mikulski et al., Efficiency of dilute sulfuric acid pretreatment of distillery stillage in the production of cellulosic ethanol, Bioresource Technol, 2018, Fol. 268: 424-433 (Year: 2018).
Taherzadeh et al., Acid-Based Hydrolysis Processes for Ethanol From Lignocellulosic Materials: a Review, BioResources, 2007, vol. 2(3); 427-499 (Year 2007).
Tenlep LG., Pretreatment Strategies for Cellulosic Ethanol, PHD Thesis, South Dakota University, 2009, pp. 1-211 (Year: 2009).
Non-Final Office Action dated Jan. 6, 2023 received in U.S. Appl. No. 17/200,053.
Non-Final Office Action dated Oct. 30, 2023 issued in U.S. Appl. No. 17/200,053

* cited by examiner

*Primary Examiner* — Ganapathirama Raghu
(74) *Attorney, Agent, or Firm* — Dorsey & Whitney LLP

(57) ABSTRACT

Processes are described herein for realizing an enhanced yield of ethanol and co-products from processes for producing ethanol from biomass containing lignocellulosic material. Also described herein are product outputs of these processes having new and useful properties and systems implementing the processes.

16 Claims, 11 Drawing Sheets

ENHANCING PRODUCT STREAMS FROM ETHANOL PRODUCTION

CROSS-REFERENCE TO RELATED APPLICATIONS TECHNICAL FIELD

This application is a continuation of U.S. patent application Ser. No. 17/200,053 entitled "ENHANCING PRODUCT STREAMS FROM ETHANOL PRODUCTION," filed on Mar. 12, 2021 which claims the benefit of U.S. Provisional Patent Application No. 62/989,423 filed Mar. 13, 2020 and entitled "ENHANCING PRODUCT STREAMS FROM ETHANOL PRODUCTION," the entire contents of both are hereby incorporated herein by reference.

TECHNICAL FIELD

The present disclosure relates generally to energy production from biomass sources. More specifically, the present disclosure relates to enhancing product and co-product yield from ethanol production processes.

BACKGROUND

The production of ethanol from biomass involves a number of unit processes, each having various inputs and losses. Whole stillage as a by-product of distillation represents a considerable process loss, particularly for ethanol production from feedstocks containing significant amounts of starch and lignocellulosic material. Whole stillage can contain unrecovered ethanol and unfermentable carbohydrates, the latter of which represent an unrealized potential yield of ethanol. The fiber content of stillage solids can also make desirable co-products of ethanol production (e.g., distillers corn oil (DCO) from corn-based ethanol production) less accessible for recovery. There is considerable interest in seizing the opportunities presented by ethanol production by-products for additional product and co-product yield. However, challenges remain in that utilization of this material to this end requires more intensive mechanical and chemical treatment, and therefore increased inputs of material resources and energy.

BRIEF DESCRIPTION OF THE FIGURES

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Reaping the potential benefits of utilizing ethanol production by-products can depend to a significant extent on the ability to recover additional ethanol and co-products from them in a cost- and resource-effective manner. In one aspect, this can involve accomplishing extra treatment steps in a more efficient manner, so that good results are achieved with a judicious use of resources. Another aspect can include increasing the useful qualities of such products and co-products. In another aspect, resource-effectiveness can be enhanced by coupling these additional recovery processes with existing production processes so as to take advantage of reusable inputs and by-products.

Processes are described herein for realizing an enhanced yield of ethanol and quality of co-products from the by-products (e.g., stillage) of existing ethanol production processes, particularly processes for producing ethanol from starch-based biomass such as corn, or other biomass comprising lignocellulosic material. Also described herein are product outputs of these processes having new and useful properties.

Reference throughout this specification to "an embodiment," "the embodiment," "particular embodiments," or "certain embodiments" means that a particular feature, structure, or characteristic described in connection with that embodiment is included in at least one embodiment. Thus, the quoted phrases, or variations thereof, as recited throughout this specification are not necessarily all referring to the same embodiment.

The phrase "operably connected to" refers to any form of interaction between two or more entities, including mechanical, electrical, magnetic, electromagnetic, fluid, and thermal interaction. Two entities may interact with each other even though they are not in direct contact with each other. For example, two entities may interact with each other through an intermediate entity.

Figure 1:
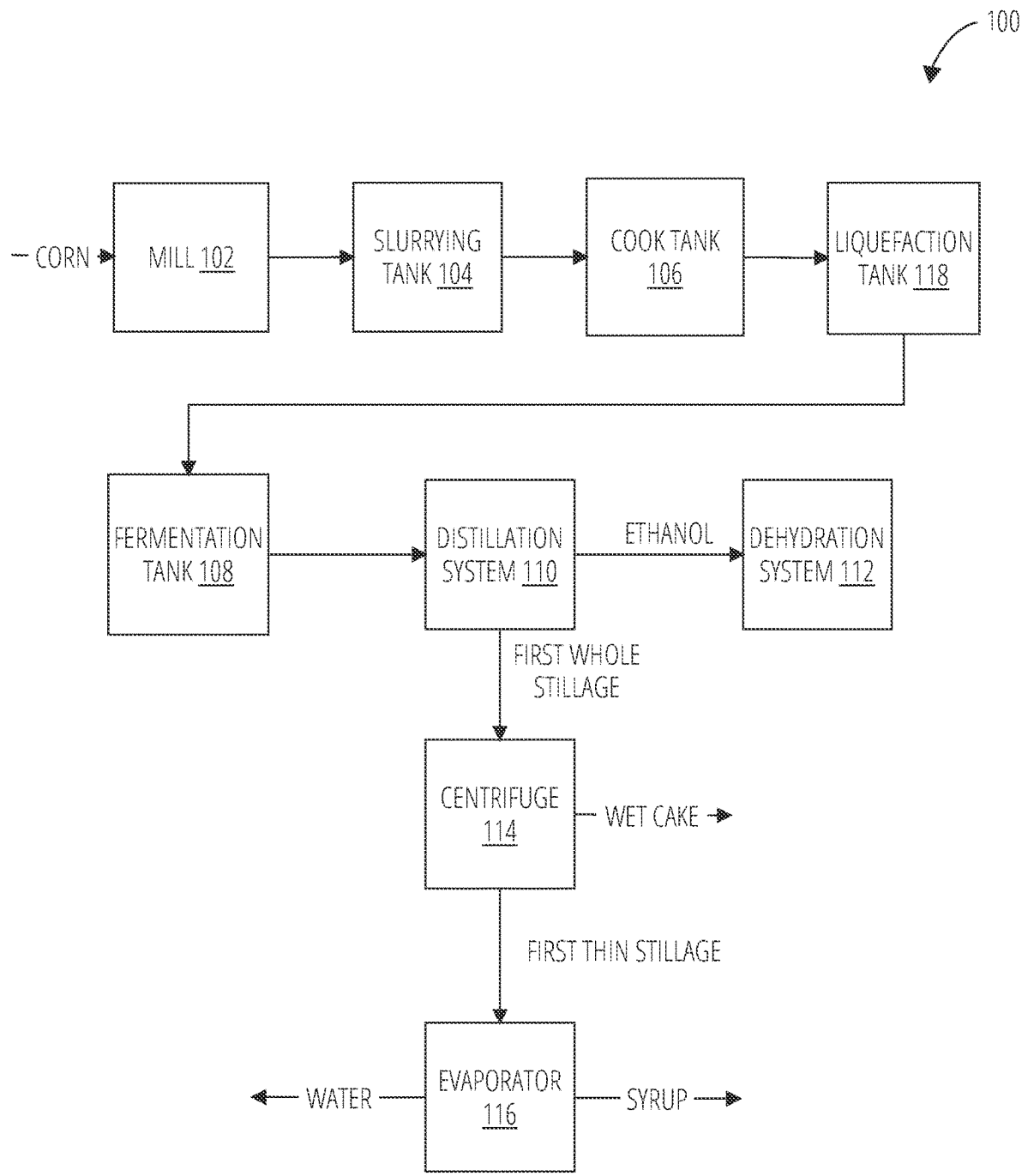
FIG. 1 illustrates an ethanol production plant 100 representative of current approaches used in the art.

As shown in FIG. 1 presenting corn-based ethanol production by way of example, an ethanol production plant 100 can comprise a plurality of unit operations and processes as follows. A corn feedstock is ground by a mill 102 to reduce the corn to particles of a selected size. In a particular embodiment, the mill 102 can employ a dry-milling process, i.e., employing mechanical means of breaking or crushing the corn kernels into smaller pieces without the addition of any liquid. Dry-milling techniques include, by way of non-limiting example, hammer milling, roller milling, and ball-milling. The fractionated corn undergoes further processes designed to make available fermentable sugars from the carbohydrates (primarily starch) in the corn. These processes can include slurrying performed in a slurrying tank 104, cooking in a cook tank 106, and liquefaction in a liquefaction tank 118. The resulting mash is transferred to a fermentation tank 108, where simple sugars produced by these processes undergo fermentation to produce ethanol. The resulting mixture of corn solids, water and ethanol, termed beer, is then sent to a distillation system 110, which strips the ethanol from the beer, yielding an ethanol solution product stream and whole stillage—mostly non-fermentable solids and water—as a by-product. Residual water is removed from the ethanol solution in one or more steps in a dehydration system 112.

The whole stillage can be further treated to recover co-products. Typically, this involves using separation equipment such as a centrifuge 114 to separate the whole stillage into its solid and liquid fractions, respectively termed hereinafter as "wet cake" and "first thin stillage" or "centrate." The wet cake can be combined with syrup produced by evaporating the thin stillage, and then dried to produce dried distillers grains with solubles (DDGS), commonly utilized in animal feed. Distillers corn oil can be extracted from the syrup produced by evaporating water from the first thin stillage, for example by using evaporator 116.

The whole stillage by-product of typical ethanol production processes, referred to herein as "first whole stillage", can contain significant amounts of polysaccharides that exited those processes in a still unfermented or unfermentable state. For example, a considerable fraction of the lignocellulosic material (cellulose, hemicellulose, and lignin) and residual starch found in corn—much of it from corn fiber—may be found in first whole stillage from corn-based ethanol production. First whole stillage, or more particularly the solid fraction thereof, can therefore be used as a feedstock for processes designed to convert these materials into sugars that can be fermented to produce an additional ethanol stream, i.e., cellulosic ethanol. The extent to which this is accomplished determines not only the additional ethanol yield from the initial feedstock, but also the characteristics of the stillage by-product of this second-generation process, which in turn influences the quality and characteristics of co-products. Other processes exist by which fermentable solids may be separated or concentrated from the by-products of primary ethanol production. It is contemplated that any such material, which can be generally termed "fermentation residual material", can be used as a feedstock for processes described herein. Therefore while the term "wet cake" is used herein by way of non-limiting example to refer to such feedstock, the discussion is intended to apply generally to fermentation residual materials.

According to the present disclosure, a method comprising a two-stage acid pretreatment process can operate on a feedstock of wet cake from primary ethanol production to effectively break up a fraction of the lignocellulosic material contained therein and convert the starch, cellulose and hemicellulose in that fraction into oligomeric and monomeric sugars.

Figure 2:
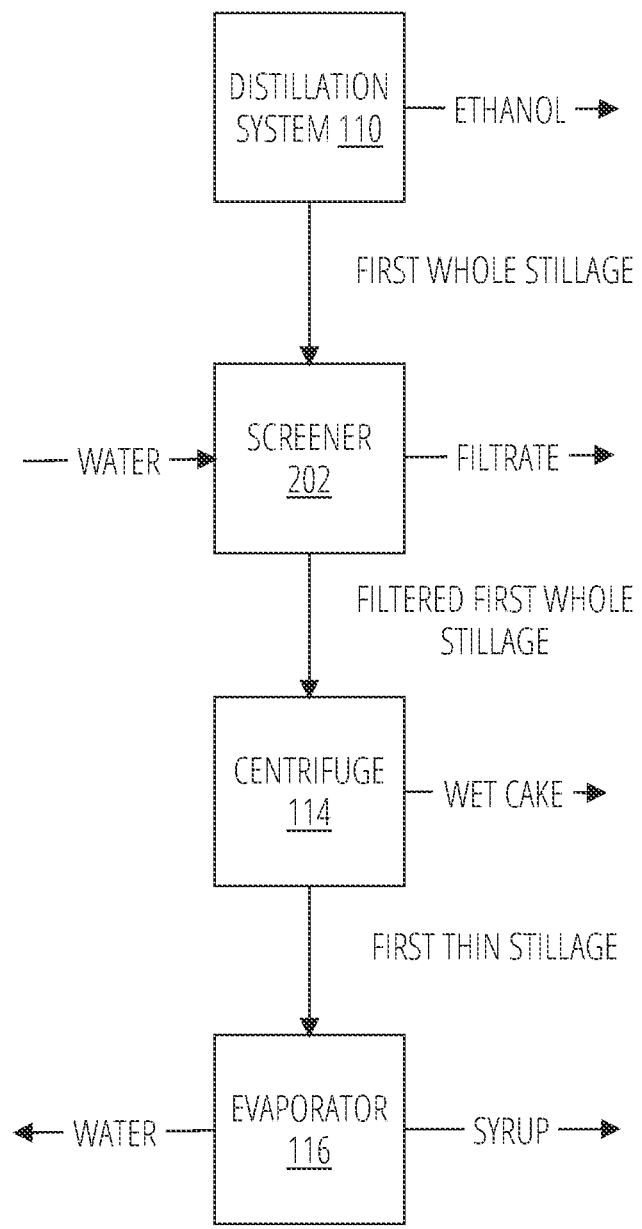
FIG. 2 illustrates a part of a primary ethanol production plant modified according to an embodiment.

In an embodiment, the composition of wet cake entering the process is modified by treating the first whole stillage stream. More specifically, protein contained in the first whole stillage is removed therefrom so as to lower the protein content of the wet cake before further processing. In accordance with the embodiment, the first whole stillage is directed to equipment configured to remove a portion of the protein contained in the first whole stillage. FIG. 2 shows part of the primary ethanol production plant illustrated in FIG. 1 modified in accordance with a particular embodiment, in which the first whole stillage from the distillation system 110 is passed—optionally with wash water—through a screener 202 configured to filter the first whole stillage so that a filtrate stream containing a portion of the protein is separated from the first whole stillage before the filtered first whole stillage enters the centrifuge 114. Equipment suitable for this purpose are known to those of skill in the art with the aid of the present disclosure. These include pressure screen devices, paddle screen devices and centrifuges with screens to allow protein to be separated which employ pressure, paddles or centrifugal force, respectively to bring a material to be filtered into contact with one or more screens by which liquid and constituents dissolved or suspended therein are separated from solids. Washing may be used to aid in the separation of protein from the whole stillage. In a specific embodiment, the screener 202 includes one or more screens each having a mesh size selected so as to separate liquid from the first whole stillage and thereby separate some of the protein from the solids. In a more specific embodiment, the screener includes a screen having a mesh size of from 100 openings/in$^2$ to 500 openings/in$^2$, or more specifically any one of 100, 150, 200, 250, 300, 350, 400, 450, or 500 openings/in$^2$. In a particular embodiment, the screener includes a plurality of stages through which the first whole stillage passes sequentially, where the plurality of stages may comprise screens of different mesh sizes.

After exiting the screener, the filtered first whole stillage is then separated by the centrifuge 114 into first thin stillage and wet cake, and the wet cake is subjected to processes such as the two-stage acid pretreatment process described below. In an aspect of these embodiments, the protein in the filtrate bypasses the two-stage acid pretreatment process and can be recovered in a downstream stage.

Figure 3:
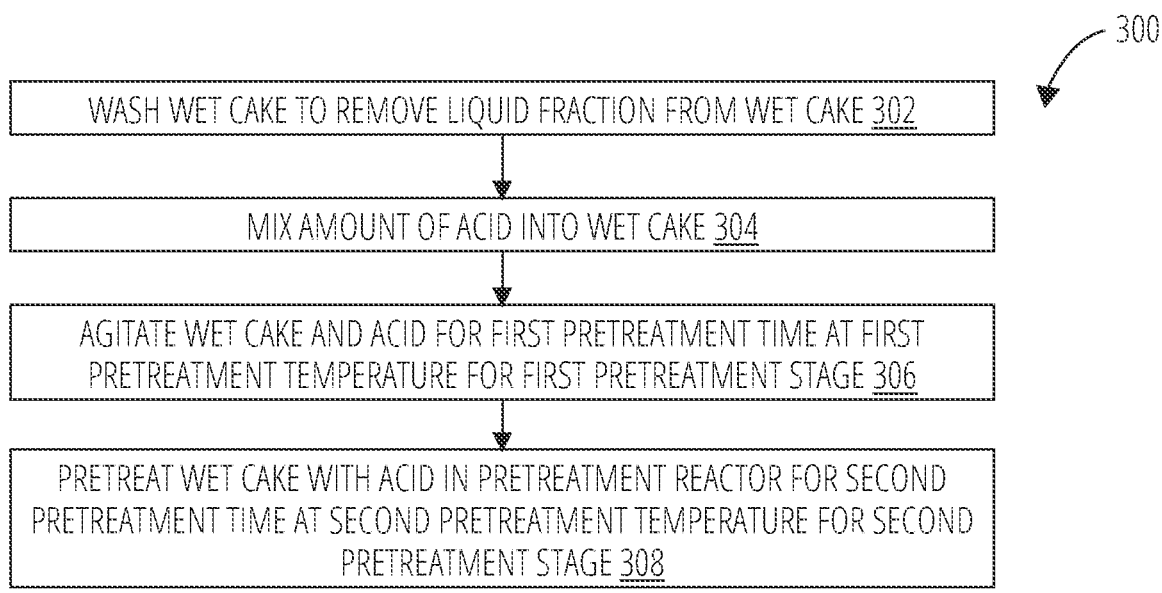
FIG. 3 illustrates a method for producing a sugar from lignocellulosic material in wet cake, in accordance with an embodiment.

In an embodiment as illustrated in FIG. 3, a method for producing sugar from lignocellulosic material in wet cake 300 can comprise a step of washing 302 the wet cake to remove a liquid fraction from the wet cake. The washing step can be accomplished in the screening step described above or employed in addition to or in alternative to the screening described above. In an acidification 304 step, an amount of an acid is mixed into the wet cake. Two stages of pretreatment are included in the embodiment, where a first pretreatment stage 306, comprises agitating the wet cake and the acid for a first pretreatment time at a first pretreatment temperature. A second pretreatment stage 308 comprises pretreating the wet cake with the acid in a pretreatment reactor for a second pretreatment time at a second pretreatment temperature.

Figure 4:
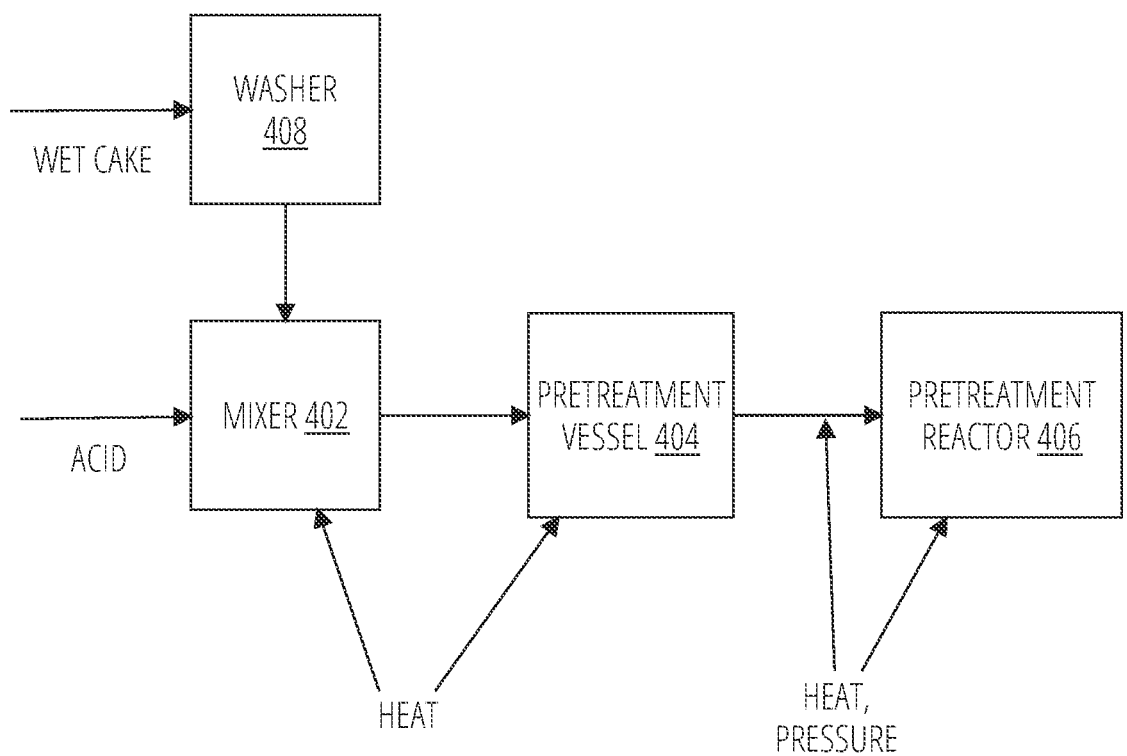
FIG. 4 illustrates a process for pretreatment of wet cake in accordance with the embodiment of FIG. 3.

This embodiment is illustrated further by way of example in FIG. 4. According to the embodiment, the method can comprise mixing an amount of an acid into the wet cake. The acid is added in an amount so that the concentration of the acid in the wet cake is from about 0.5 wt % to about 7 wt %. The acid may be added in an amount so as to achieve a pH of the wet cake of from about 1.5 to about 2.5. The acid can be added to the wet cake and mixed therewith using mechanical systems to achieve thorough mixing. In one embodiment, as illustrated in FIG. 4, a mixer 402 designed for mixing high viscosity fluids, also known as a pug mill mixer or mingler, can be used for this purpose. By way of non-limiting example, the acid used can be a mineral acid such as sulfuric, phosphoric, hydrochloric, hydrofluoric, formic, or nitric acid, or a mixture thereof, or an organic acid such as maleic, oxalic, acetic, or fumaric acid, or a mixture thereof. As would be apparent to those having skill in the art with the aid of the present disclosure, other acids may be used to decrease the pH of the wet cake in accordance with present embodiment.

In accordance with the embodiment, the first pretreatment stage can comprise heating and agitating the acidified wet cake to begin hydrolysis of the lignocellulosic material in the wet cake. Heating may not be necessary if the wet cake is already at a sufficiently high temperature. In a particular embodiment, the acidified wet cake can be transferred to a pretreatment vessel 404 for this purpose. In a more particular embodiment, this vessel is a cone-bottomed tank equipped with an agitator, where agitation of the material is performed for a first pretreatment time. In other embodiments, a horizontal or vertical pipe could be used for this step. In a particular embodiment, the acidified wet cake is heated before it is transferred to the pretreatment vessel 404, for example while it is in the mixer 402. In another embodiment, the acidified wet cake is heated in the pretreatment vessel 404.

In a particular aspect of the two-stage acid pretreatment process, this first pretreatment stage is accomplished without employing high pressures. In a particular embodiment, the first stage is conducted with the acidified wet cake at a first pretreatment pressure that is from slightly negative (about −1 psig) to about 10 psig. According to more specific embodiments, the first pretreatment pressure can be from about −1 psig to about 5 psig, or from 0 psig to about 6 psig, or from 0 psig to about 10 psig.

The wet cake is heated to a first pretreatment temperature for the first stage of pretreatment. This can be done during acidification in the mixer 402 or during agitation in the pretreatment vessel 404. Alternatively, the wet cake may be hot (e.g., 170° F. or above) as it exits from the first whole stillage decanter and therefore may not need to be heated further. In a particular embodiment, the first pretreatment temperature is from about 170° F. to about 225° F. According to more specific embodiments, the first pretreatment temperature is from about 180° F. to about 215° F., or from about 190° F. to about 200° F., or from about 170° F. to about 200° F., or from about 180° F. to about 225° F. In a particular embodiment, the first pretreatment pressure is at atmospheric pressure and the boiling temperature of pure water at the elevation at which this step is conducted is the upper limit for the first pretreatment temperature.

The first pretreatment time can be selected so as to achieve thorough mixing of the acid and wet cake based on the mass of wet cake resident in this step. In a particular embodiment, the first pretreatment time can be from about 10 minutes to about 300 minutes. In more specific embodiments, the first pretreatment time can be from about 30 minutes to about 180 minutes, or about 20 minutes to about 120 minutes, or from about 5 minutes to about 90 minutes, or from about 15 minutes to about 60 minutes.

The inventors have surprisingly found that, despite employing relatively low pressure and temperature, the first pretreatment stage achieves effective hydrolysis of cellulose and hemicellulose to a desired yield of soluble sugars (e.g., glucose, xylose, galactose, arabinose, and mannose). In an embodiment, the first pretreatment stage provides a percent yield of soluble glucose of from about 10% to about 60%, or an average percent yield of from about 30% to about 45%. In a more particular embodiment, the percent yield of monomeric glucose from the first stage is from about 0% to about 10%, or an average percent yield of from about 1% to about 4%. In another embodiment, the first pretreatment stage provides a percent yield of soluble xylose of from about 80% to about 100%, or an average percent yield of from about 93% to about 97%. In a more particular embodiment, the yield of monomeric xylose from the first stage is from about 0% to about 25%, or an average percent yield of from about 5% to about 10%. In another embodiment, the first pretreatment stage provides a percent yield of soluble arabinose of from about 85% to about 100%, or an average percent yield of about 95% to about 99%. In a more particular embodiment, the yield of monomeric arabinose from the first stage is from about 0% to about 95%, or an average percent yield of about 45% to about 60%. In still another embodiment, the first pretreatment stage provides a percent yield of soluble galactose of from about 55% to about 100%, or an average percent yield of about 90% to about 95%. In a more particular embodiment, the yield of monomeric galactose from the first stage is from about 0% to about 50%, or an average percent yield of about 10% to about 20%. In still another embodiment, the first pretreatment stage provides a percent yield of soluble mannose of from about 30% to about 100%, or an average percent yield of about 75% to about 90%. In a more particular embodiment, the yield of monomeric mannose from the first stage is from about 0% to about 75%, or an average percent yield of about 10% to about 25%.

In another aspect of the two-stage acid pretreatment process, in addition to effective conversion of lignocellulosic material to sugars, the production of unfermentable compounds that can arise from the degradation of these sugars (e.g., furfural and hydroxymethylfurfural from degradation of xylose and glucose, respectively) is minimized. The different parameters of this process—residence time, pH, and temperature—combine to influence these outcomes. Generally, addition of less acid will involve conducting this stage at higher temperature and/or for longer residence time in order to achieve similar results compared to a higher acid concentration. Therefore, in accordance with the present disclosure, the pH of the wet cake and length of the first pretreatment time and the first pretreatment temperature can be selected to achieve desired results. In one example, the first pretreatment stage can be done by selecting a higher pH (i.e., adding less acid) in combination with a higher first pretreatment temperature, a longer first pretreatment time, or both. In another example, a lower pH is selected in combination with a lower first pretreatment temperature, a shorter first pretreatment time, or both. In still another example, higher pH and lower first pretreatment temperature can be employed with a longer first pretreatment time. In another example, a lower pH can be selected in combination with a lower first pretreatment temperature and a longer first pretreatment time.

One aspect of the pretreatment process is that mixing and the selection of temperature and time can allow for more complete hydrolysis by a given amount of acid added to the wet cake. Therefore, one potential result is a decrease in the amount of acid required to achieve desired yields of fermentable sugars. In one aspect, this provides for more efficient use and less waste of acid. The amount of acid can be selected so as to minimize undesired downstream effects. For example, one may seek to decrease the amount of sulfur in dried distillers grains produced by this method by managing the amount of sulfuric acid used in pretreatment.

The content of solids and liquids in wet cake can influence the effectiveness of acid in pretreatment. That is, a higher liquid content may dilute or buffer the added acid or otherwise reduce the amount of interaction between the acid and the lignocellulosic material in the wet cake. In a particular embodiment, preparation of wet cake for acidification can include bringing its solids content to a level of from about 15 wt % to about 40 wt %, or more particularly from about 20 wt % to about 35 wt %. In a specific embodiment, acidification can be preceded by washing the wet cake in a washer 408 to remove a portion of the liquid fraction of the wet cake and thereby achieve a desired solids content in the wet cake. The washing can also have the benefit of reducing the buffering capacity of the wet cake, or more particularly the liquid fraction of the wet cake. Washing can be done with water or other aqueous liquid. In a specific embodiment, liquid reclaimed from other unit processes or a by-product of such processes, such as condensate from evaporation of first thin stillage, can be used for this step. In an aspect of this embodiment, the liquid fraction removed from the wet cake is substantially replaced by a non-buffering, low pH liquid (the condensate).

To facilitate further hydrolysis of cellulose and hemicellulose to fermentable sugars, after the first pretreatment time has concluded a second pretreatment stage can comprise directing the wet cake to a pretreatment reactor 406, wherein the wet cake is subjected to a higher temperature and a higher pressure than those employed in the first pretreatment stage. In a particular embodiment, the wet cake is heated to a second pretreatment temperature higher than the first pretreatment temperature used in the first stage and held substantially at that temperature for a second pretreatment time. In a particular embodiment, the second pretreatment temperature is from about 230° F. to about 330° F. According to more specific embodiments, the second pretreatment temperature can be from about 245° F. to about 320° F., or from about 250° F. to about 300° F., or from about 270° F. to about 300° F., or from about 230° F. to about 310° F. In a more particular embodiment, the wet cake is also subjected to a second pretreatment pressure that is higher than the first pretreatment pressure. Higher pressures at this stage may be employed to maintain a sufficiently high wet cake temperature.

Heating at this stage can be accomplished by steam injection, or other heating methods as will be recognized by those of skill in the art with the aid of the present disclosure. In a particular embodiment, the wet cake is heated before it is transferred to the pretreatment reactor 406, for example by steam injection in transit to the pretreatment reactor 406. In another embodiment, the acidified wet cake is heated in the pretreatment reactor 406. As with the first stage, the results of the second pretreatment stage can be influenced by the particular combination of wet cake pH, second pretreatment temperature, and second pretreatment time. As such, the second pretreatment temperature and second pretreatment time can be selected in view of the amount of acid added during acidification so as to enhance the yield of soluble sugars and minimize the creation of degradation products.

The high yield of soluble sugars in the first pretreatment stage allows operation of the pretreatment reactor 406 at lower temperatures and pressures than might otherwise be required to achieve similar yields of oligomeric and monomeric sugars. In this way the capital cost and energy expenditure of pretreatment may be reduced. Lower pretreatment temperatures also reduce the amount of undesirable sugar degradation products produced, improving the efficiencies of downstream enzymatic hydrolysis and fermentation steps. The commencement of hydrolysis in the first stage also allows for a relatively short second pretreatment time. In a particular embodiment, the second pretreatment time can be from about 3 minutes to about 100 minutes. According to more specific embodiments, the second pretreatment time can be from about 3 minutes to about 50 minutes, or about 30 minutes to about 80 minutes, or from about 5 minutes to about 8 minutes, or from about 20 minutes to about 50 minutes. However, it will be understood that a single pretreatment stage, e.g., the second pretreatment stage, can alternatively be relied upon to produce sugars from lignocellulosic material in the wet cake in accordance with the present disclosure.

From the present disclosure and the illustration in FIG. 4, it will be appreciated that a system for pretreating wet cake to produce sugar from lignocellulosic material contained therein can comprise a mixer 402 configured to receive an acid and to receive wet cake, and to mix the acid into the wet cake to produce an acidified wet cake; a pretreatment vessel 404 operably connected to the mixer 402 and configured to receive the acidified wet cake from the mixer 402 and agitate the acidified wet cake at a first pretreatment temperature and a first pretreatment pressure; and a pretreatment reactor 406 operably connected to the pretreatment vessel and configured to receive the acidified wet cake from the pretreatment vessel and react the acidified wet cake at a second pretreatment temperature and a second pretreatment pressure. The pretreatment reactor 406 can be a reactor designed to operate at the temperature and pressures discussed above. In a particular embodiment, the reactor is designed so that substantially the entire volume of acidified wet cake is uniformly exposed to the second pretreatment temperature over the second pretreatment time. Possible reactor configurations include one or more continuous stirred reactors in series, one or more batch reactors, or a horizontal or vertical vessel or pipe. In a specific embodiment, the pretreatment reactor 406 is a plug flow reactor. As described above, the pretreatment vessel 404 can be a cone-bottomed tank equipped with an agitator, or a horizontal pipe or vertical pipe.

In the second pretreatment stage additional polysaccharides in the acidified wet cake are converted to oligomers and monomers, and oligomeric sugars entering this stage are converted to monomers and smaller oligomers. In an embodiment, the second pretreatment stage provides a percent yield of soluble glucose of from about 10% to about 60%, or an average percent yield of about 35% to about 45%. In a more particular embodiment, the yield of monomeric glucose from the second stage is from about 0% to about 30%, or an average percent yield of about 5% to about 10%. In another embodiment, the second pretreatment stage provides a percent yield of soluble xylose of from about 50% to about 100%, or an average percent yield of about 90% to about 95%. In a more particular embodiment, the yield of monomeric xylose from the second stage is from about 0% to about 65%, or an average percent yield of about 20% to about 30%. In another embodiment, the second pretreatment stage provides a percent yield of soluble arabinose of from about 40% to about 100%, or an average percent yield of about 85% to about 95%. In a more particular embodiment, the yield of monomeric arabinose from the second pretreatment stage is from about 20% to about 100%, or an average percent yield of about 65% to about 75%. In still another embodiment, the second pretreatment stage provides a percent yield of soluble galactose of from about 55% to about 100%, or an average percent yield of about 85% to about 95%. In a more particular embodiment, the yield of monomeric galactose from the second stage is from about 2% to about 100%, or an average percent yield of about 35% to about 45%. In still another embodiment, the second pretreatment stage provides a percent yield of soluble mannose of from about 30% to about 100%, or an average percent yield of about 75% to about 85%. In a more particular embodiment, the yield of monomeric mannose from the second stage is from about 0% to about 100%, or an average percent yield of about 20% to about 30%.

Figure 5:
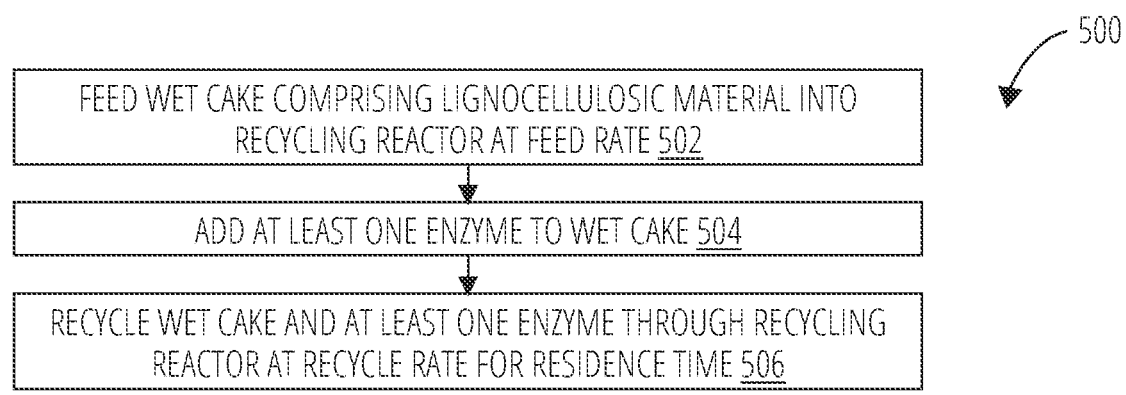
FIG. 5 illustrates a method for hydrolyzing lignocellulosic material in wet cake, in accordance with one embodiment.

Saccharification can then be performed on the pretreated wet cake, comprising using enzymatic hydrolysis to produce further monomeric sugars from oligosaccharides and polysaccharides remaining after the two-stage acid pretreatment process. In an embodiment as shown in FIG. 5, a method of hydrolyzing lignocellulosic material in wet cake 500 can comprise: feeding 502 wet cake comprising lignocellulosic material into a recycling reactor at a feed rate; enzyme addition 504, in which at least one enzyme is added to the wet cake; and recycling 506 the wet cake and at least one enzyme through the recycling reactor at a recycle rate and for a residence time to hydrolyze the lignocellulosic material to produce an amount of monomeric sugar in the wet cake.

Figure 6:
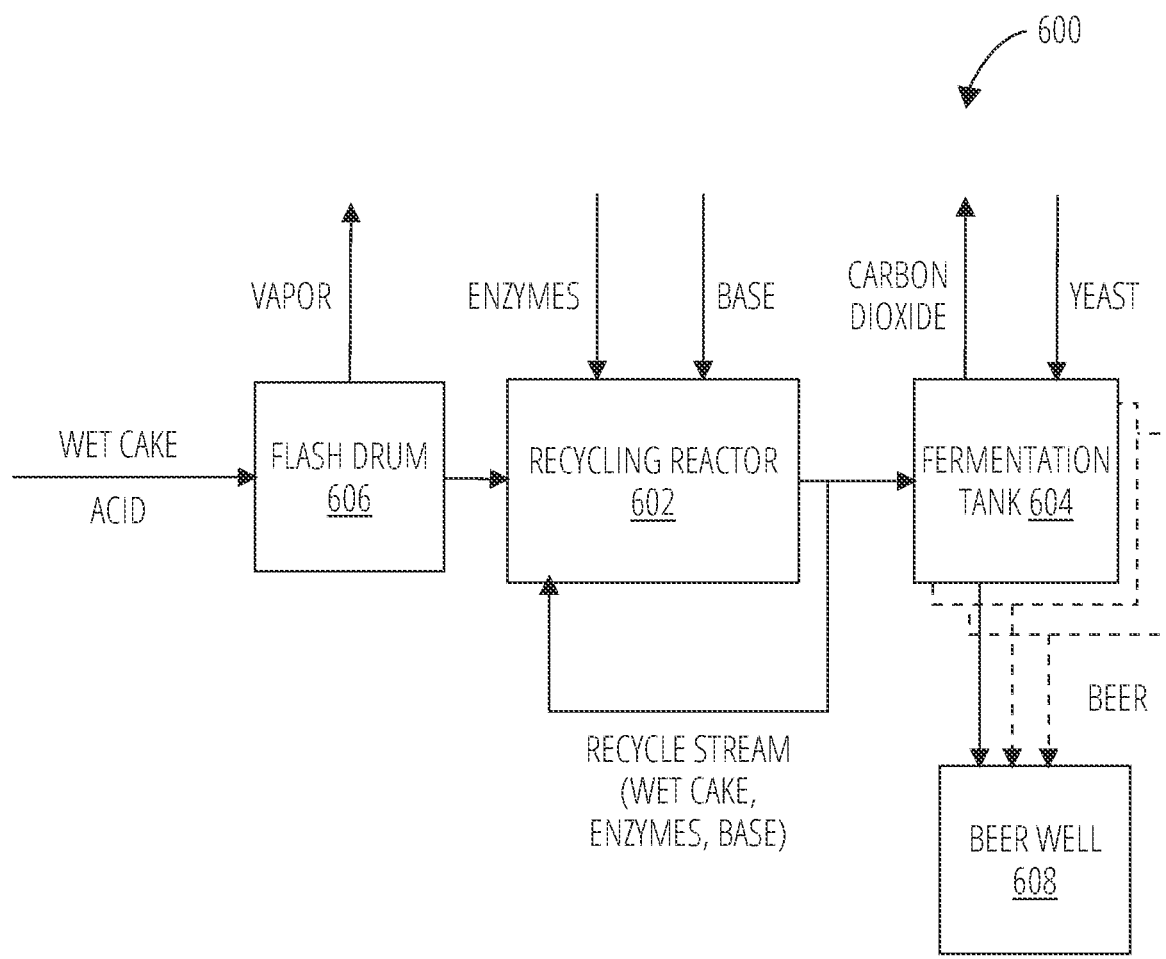
FIG. 6 illustrates a process for enzymatic hydrolysis in accordance with the embodiment of FIG. 5.

The embodiment as illustrated further by way of example in FIG. 6. According to the embodiment, the process can comprise feeding the acidified wet cake into a recycling reactor 602 at a feed rate and adding one or more enzymes selected to act upon the oligosaccharides and polysaccharides. As will be appreciated by those of skill in the art with the aid of this disclosure, enzymes known to be effective at breaking up oligosaccharides and lignocellulosic material can be used in this process, and include various cellulases and hemicellulases, as well as amylase and beta-glucosidase. More specifically, hemicellulases can include xylanase, mannase, galactidase, and arabinase. To facilitate activity of the enzyme(s), the pH of the wet cake can also be increased by the addition of a basic solution, either before or after the wet cake enters the recycling reactor 602. Bases that can be used in this step include, without limitation, ammonia, aqua ammonia, sodium hydroxide, sodium bicarbonate, potassium hydroxide, potassium carbonate, calcium hydroxide, and magnesium hydroxide. Other suitable bases for use in this step will be apparent to those of skill in the art having the benefit of this disclosure. The wet cake can first be cooled if needed to bring it to a temperature at which the selected enzyme(s) will have the desired level of activity. As illustrated in FIG. 6, cooling can be performed by flashing a vapor off of the wet cake in a flash drum 606. As will be appreciated by those of skill in the art with the aid of this disclosure, other approaches and equipment suitable for cooling wet cake can be employed in addition or in alternative to flashing, including without limitation, multiple flash steps and passing the wet cake through one or more heat exchangers.

The process can continue with recycling the wet cake repeatedly through the recycling reactor 602 for a selected residence time, during which the enzyme(s) is mixed substantially uniformly throughout the volume of wet cake and begins to hydrolyze the oligosaccharides and lignocellulosic material. In a particular embodiment, the recycling reactor 602 is operated at a recycle rate that is higher than the mass flow rate at which the wet cake is fed into the recycling reactor 602. In an embodiment, the recycle rate is from about 1 to about 10 times the feed rate. In a more specific embodiment, the recycle rate is from about 5 to about 10 times the feed rate. In a still more specific embodiment, the recycle rate is from about 3 to about 6 times the feed rate. In another specific embodiment, the recycle rate is from about 1 to about 5 times the feed rate.

Outcomes from recycling the wet cake include, but are not limited to, reducing the viscosity of the wet cake entering the recycling reactor 602 due to dilution; 2) aiding reduction of the temperature of the wet cake to a target temperature for enzymatic activity; and 3) effective mixing of the enzyme(s) into the wet cake. In a particular embodiment, the wet cake has a viscosity from 250 cp to 3000 cp upon exiting the recycling reactor 602. In a more specific embodiment, the wet cake has a viscosity of from 500 cp to 2000 cp. In one aspect, the effective mixing allows for using cost-effective amounts of enzymes.

The residence time during which a volume of wet cake and enzyme(s) is present in the reactor can be selected to be sufficient to achieve the above objectives. In a particular embodiment, the residence time is from about 6 hours to about 15 hours. In more particular embodiments, the residence time is from about 10 hours to about 13 hours, or from about 12 hours to about 15 hours, or more particularly from about 11 hours to about 13 hours. In a particular embodiment, the enzymatic hydrolysis process is a flow-through process, where the feed rate, recycle rate, and residence time are selected so that each unit volume of wet cake entering the reactor undergoes substantially similar processing conditions.

From the present disclosure and the illustration in FIG. 6, it will be appreciated that a system 600 for saccharification of lignocellulosic material in wet cake can comprise a recycling reactor 602 configured to receive wet cake, such as from the flash drum 606, and at least one enzyme and allow for reaction between the same. The recycling reactor 602 can be further configured to receive a recycle stream of the wet cake and enzyme(s) at a recycle rate that is greater than the feed rate. In a particular embodiment, the recycle rate is from about 1 to 10 times the feed rate. In a more specific embodiment, the recycle rate is from 1 to 3 times the feed rate. In a still more specific embodiment, the recycle rate is from 2 to 4 times the feed rate. The system 600 can include a pump operably connected to the recycling reactor 602 that provides circulation of the recycle stream at the recycle rate. The recycling reactor 602 can be further configured to receive a base and to combine the base and the wet cake.

The residence time may be sufficient for enzymatic hydrolysis to begin, yet it need not be long enough to complete said hydrolysis. Rather, after initial hydrolysis the wet cake and enzymes may be transferred to a fermentation tank 604 where further hydrolysis occurs prior to starting fermentation. Prior to starting fermentation, the temperature of the wet cake is reduced from the hydrolysis temperature (typically in the range of about 120° F. to 150° F.) to the optimum fermentation temperature (typically about 95° F.). Hydrolysis continues at a slower rate during fermentation.

In some embodiments, the pretreated wet cake is transferred to one of a plurality of saccharification tanks. The wet cake can first be cooled if needed to bring it to a temperature at which the selected enzyme(s) will have the desired level of activity. The pH in the saccharification tank is adjusted if needed and enzymes are added. In a particular embodiment, the plurality of saccharification tanks are functionally connected in series to perform saccharification in a serial manner, wherein enzymatic hydrolysis is allowed to proceed for a time in the first saccharification tank, after which the wet cake is transferred to another saccharification tank in the series for further enzymatic hydrolysis. This transferring step is repeated with the remaining saccharification tanks in the series, after which the wet cake and enzymes are transferred to the fermentation tank 604. In a specific embodiment, the series can include the recycling reactor 602, into which the pretreated wet cake is transferred and in which enzymatic hydrolysis begins before the wet cake is transferred to the first saccharification tank. In an aspect, the size and number of saccharification tanks can be adjusted to provide a desired total residence time. In a specific embodiment, the total residence time is from about 35 hours to about 55 hours. In a more specific embodiment, the total residence time is about 40 hours.

In another particular embodiment, the plurality of saccharification tanks are configured in parallel to perform saccharification in a batch manner, wherein a batch of pretreated wet cake is transferred to one of the saccharification tanks in which the pH is adjusted if needed, enzymes are added, and enzymatic hydrolysis proceeds for a residence time, and then the wet cake and enzymes are transferred to the fermentation tank 604. Another batch of pretreated wet cake can be transferred into another one of the saccharification tanks to undergo the same or a similar process. In a more particular embodiment, saccharification comprises using at least three saccharification tanks cycling at intervals, for example where one or more saccharification tanks are holding wet cake undergoing hydrolysis, while one or more of the other saccharification tanks are being filled with pretreated wet cake, and one or more of the remaining saccharification tanks are transferring wet cake and enzymes to the fermentation tank 604. In an aspect, each saccharification tank can be sized so as to hold the wet cake and enzymes for a desired residence time. In a specific embodiment, the residence time is from about 35 hours to about 55 hours. In a more specific embodiment, the residence time is about 40 hours.

Fermentation creates cellulosic ethanol and carbon dioxide from the sugars in the wet cake. To commence this step, an ethanol-producing microbe is added to the wet cake. It will be appreciated by those skilled in the art in view of the present disclosure that one or more of any ethanol-producing microbes, including native and genetically modified microbes, may be used, such as *Zymomonas mobilis, Saccharomyces cerevisiae, Escherichia coli, Bacillus subtilis*, and *Pichia pastoris*. As indicated above, enzymatic hydrolysis of remaining polysaccharides and oligosaccharides begun in the previous step may continue in the fermentation tank 604. In an aspect of the embodiment, the contemporaneous fermentation of sugars in the wet cake may promote more complete hydrolysis of the polysaccharides by decreasing end-product inhibition of the hydrolysis reactions.

According to one embodiment, hydrolysis and fermentation of wet cake exiting the recycling reactor 602 may be done in batches among a number of tanks so that adjacent processes can operate continuously, if desired. To accommodate the beer output stream from the fermentation tank 604 and to facilitate controlled delivery to subsequent processes, a batch of beer produced in fermentation tank 604 can be collected in a beer well 608. Carbon dioxide and other vapor streams may be collected from the fermentation tank(s) and the beer well 608 and scrubbed using techniques known in the art to remove ethanol and other components entrained in the vapor.

Figure 7:
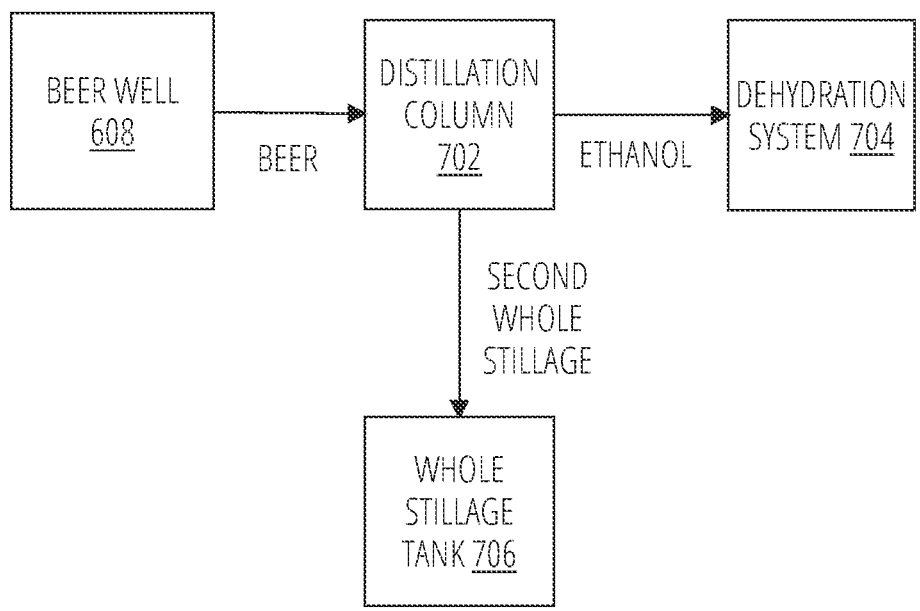
FIG. 7 illustrates an exemplary process for recovering cellulosic ethanol in accordance with an embodiment.

Ethanol can be recovered from the beer using any number of techniques and equipment known in the art to be suitable for this purpose. More particularly, typical techniques, generally termed distillation, involve separating the liquid and solid components by initiating the transition of the liquid component to vapor, which is then condensed and collected. Typically, the initial output of this process is a mixture of ethanol, water, and other volatile components. Further steps can be performed on this mixture to separate ethanol from the other components, typically by making use of differences in their respective volatilities. A cellulosic ethanol production process is illustrated in FIG. 7, in which the beer produced by fermentation is transferred from the beer well 608 to a distillation column 702 to produce a cellulosic ethanol stream and also a whole stillage by-product, referred to herein as "second whole stillage", comprising the nonvolatile components of the beer. In a particular embodiment, the second whole stillage is collected into a whole stillage tank 706. In an aspect of the embodiment, the whole stillage tank 706 can be equipped with an agitator.

As will be appreciated by those having skill in the art, the percentage of ethanol and water in the cellulosic ethanol stream after a single distillation will depend upon many variables, including the type, length, efficiency, and pressure of the column. The cellulosic ethanol stream can be directed to a dehydration system 704 to remove water and other non-ethanol volatile components. In a particular embodiment, dehydration can comprise sending the cellulosic ethanol stream through either or both of a rectification column, and one or more molecular sieves. In another embodiment, dehydration can comprise sending the cellulosic ethanol stream through a membrane separation system, in which a pervaporation membrane is used to separate water and ethanol through differential permeation.

Figure 8:
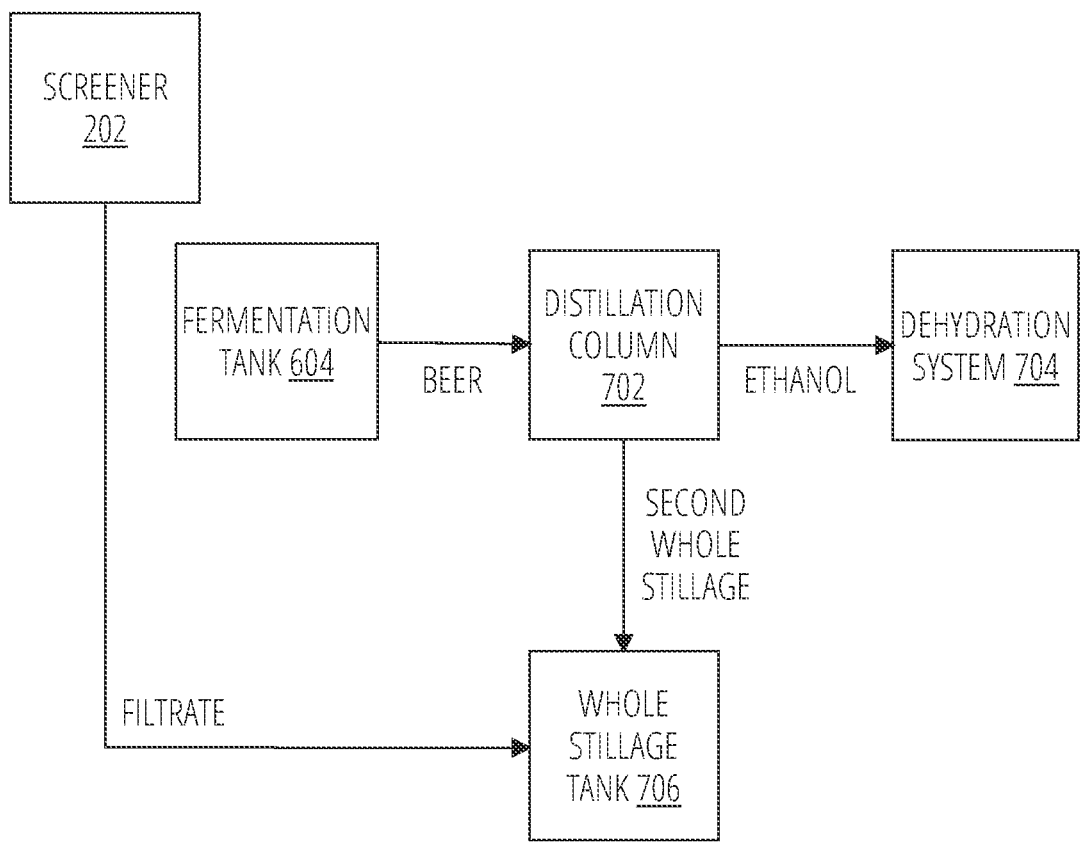
FIG. 8 illustrates an exemplary process for recovering cellulosic ethanol modified in accordance with the embodiment shown in FIG. 2.

The second whole stillage can exhibit particular characteristics that distinguish it from the first whole stillage produced by primary ethanol production. In one embodiment, as a result of the pretreatment and saccharification processes of the present disclosure, most or all of the carbohydrates in the lignocellulosic material in the wet cake feedstock is converted to fermentable sugars, which are then converted to ethanol in fermentation. Therefore, the second whole stillage by-product of the present disclosure comprises low weight percentages of residual fiber, starch, and cellulose and a high percentage weight of crude protein. In a particular embodiment, the second whole stillage has a percent by weight of crude protein from about 40% to about 55%. In more specific embodiments, crude protein content of the second whole stillage is from about 40 wt % to about 50 wt %, or from about 35 wt % to about 55 wt %, or from about 35 wt % to about 50 wt %. In another particular embodiment as shown in FIG. 8, protein is filtered from the first whole stillage in the screener 202 into a filtrate stream as described above and the filtrate stream is combined with the second whole stillage in the whole stillage tank 706. Agitation can be employed in the whole stillage tank 706 to provide thorough mixing of the filtrate into the second whole stillage. One result of the processes described herein is that protein (both plant protein and yeast or other microbes) will constitute a significant percentage of the total mass of the second whole stillage, making it a good source material for production of high-protein dried distillers grains and other products derived therefrom.

Figure 9:
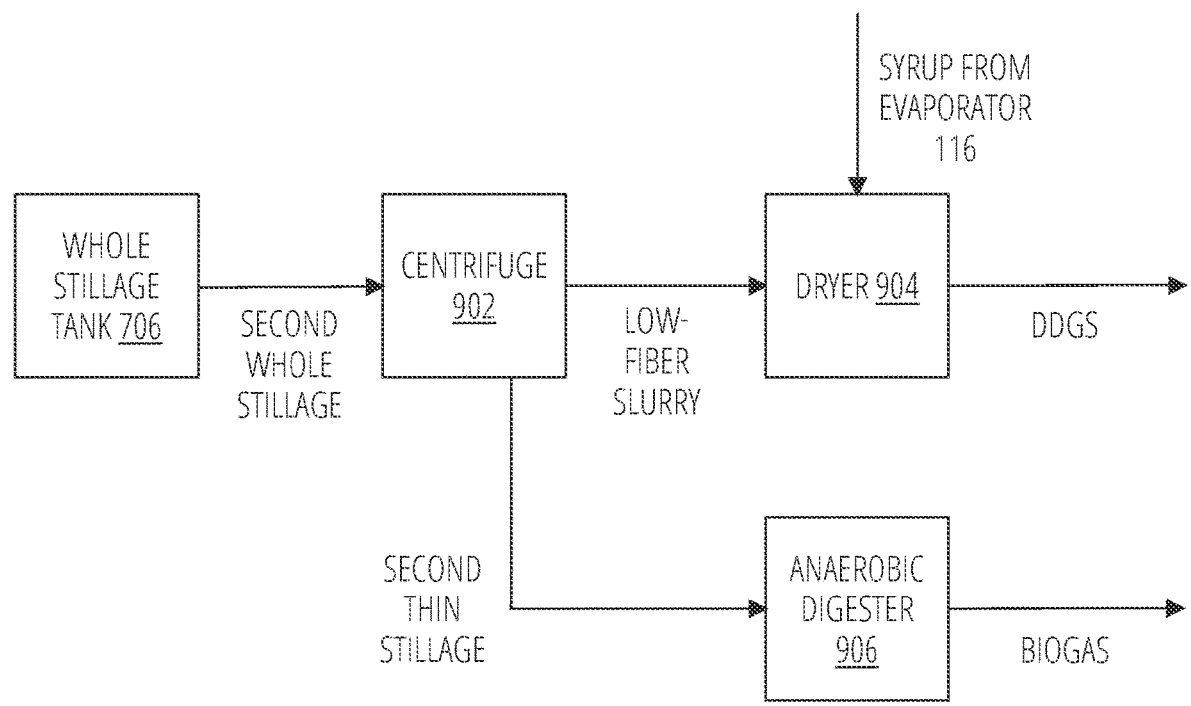
FIG. 9 illustrates a process for co-product production from fermented wet cake in accordance with an embodiment.

In accordance with the present disclosure, co-product production from the second whole stillage can comprise separating the second whole stillage into its liquid and solid components. Separation techniques and equipment suitable for this process are well-known in the art. In one embodiment, the second whole stillage can be processed using the same or similar approaches as are used in primary ethanol production plants. In an exemplary embodiment as shown in FIG. 9, the second whole stillage can be fed from the whole stillage tank 706 into a centrifuge 902, such as a decanter centrifuge, which separates the second whole stillage into a semi-solid low-fiber slurry and a thin stillage (termed hereinafter as "second thin stillage"). A dryer 904 can be used to remove residual moisture from the resulting low-fiber slurry, thereby producing a dried distillers grains (DDG) having a high protein content.

Dried distillers grains with solubles (DDGS) can be made by recombining syrup (produced from the evaporation of first thin stillage) with wet distillers grains before drying. Accordingly, it is contemplated that syrup produced from the evaporation of both first thin stillage and second thin stillage can be combined with the low-fiber slurry in making DDGS in accordance with the present disclosure. However, the inventors have surprisingly found that a higher quality DDGS may be attainable when the low-fiber slurry of the present disclosure is dried without the addition of the second thin stillage. In this embodiment, syrup produced from the first thin stillage from the primary ethanol production plant evaporator 116 is still mixed with the low-fiber slurry prior to drying, but without inclusion of the second thin stillage or syrup produced therefrom.

In certain embodiments, the DDGS in accordance with the present disclosure has a total protein content of from about 40 wt % to about 70 wt %. In a more particular embodiment, the DDGS has a total protein content of from about 50 wt % to about 65 wt %. In other particular embodiments the total protein content can be from about 45 wt % to about 55 wt %, or from about 40 wt % to about 60 wt %, or from about 50 wt % to about 70 wt %. In an aspect of these embodiments, the DDGS also has a low fiber content due to the extent of breakdown and conversion of the fiber in the wet cake feedstock by the two-stage acid pretreatment process and the enzymatic hydrolysis process of the present disclosure. In a more specific aspect, the DDGS comprises fiber in an amount from about 0.5 wt % to about 2 wt %. The DDGS in accordance with the present disclosure can also include particular nutrients of interest in animal health. In one aspect, the DDGS contains glutamic acid in an amount from about 6 wt % to about 10 wt %, or more specifically from about 7 wt % to about 9 wt %. In another aspect, the DDGS contains aspartic acid in an amount from about 1 wt % to about 5 wt % or more specifically from about 2 wt % to about 4 wt %. In another aspect, the DDGS contains alanine in an amount from about 2 wt % to about 5 wt % or more specifically from about 3 wt % to about 4 wt %. In another aspect, the DDGS contains vitamin A in an amount from about 800 I.U./kg and about 1200 I.U./kg, or more specifically from about 900 I.U./kg to about 1100 I.U./kg. In another aspect, the DDGS contains vitamin E in an amount from about 450 I.U./kg and about 650 I.U./kg, or more specifically from about 400 I.U./kg to about 600 I.U./kg.

In another aspect, a low fiber content in the DDGS of the present disclosure gives it enhanced digestibility and digestible energy. In a particular aspect, the DDGS has a digestible energy content of at least 1500 kcal/lb. In a more specific aspect, digestible energy content is from 1500 kcal/lb to about 2000 kcal/lb. In another aspect, low fiber content imparts particular physical characteristics, such as a fine consistency and higher density. In a particular embodiment the DDGS has a density of from about 30 lbs/ft$^3$ to about 40 lbs/ft$^3$, or more specifically from about 34 lbs/ft$^3$ to about 38 lbs/ft$^3$, or from about 30 lbs/ft$^3$ to about 35 lbs/ft$^3$, or from about 34 lbs/ft$^3$ to about 40 lbs/ft$^3$.

As noted above, rather than recombination with the low-fiber slurry to produce DDGS for animal feed, the second thin stillage can be directed to other uses. In co-product production, the second thin stillage can be directed to an evaporator, where evaporation of water from the second thin stillage can proceed until the second thin stillage becomes a syrup, or further to produce a substantially solid material, either of which can be used as an animal feed additive. In a particular embodiment, the second thin stillage stream is combined with the first thin stillage stream for evaporation in the same evaporator, e.g., evaporator 116. Alternatively, as shown in FIG. 9, the second thin stillage can be directed to an anaerobic digester 906, where anaerobic digestion can be performed on the second thin stillage to produce a biogas which can be scrubbed and added to existing natural gas pipelines or the biogas can be used in the primary ethanol plant's boiler. This approach may be undertaken as an effective way to remove the chemical oxygen demand of the second thin stillage.

Another aspect of the present disclosure with respect to corn-based ethanol production processes is that with less fiber to bind corn oil contained in the second whole stillage by-product, more of the corn oil is decanted off into the second thin stillage. Accordingly, in one embodiment a distillers corn oil stream can be obtained from the second thin stillage. In a particular embodiment, the second thin stillage is combined with the first thin stillage for further processing, e.g., evaporation to produce a syrup from which distillers corn oil is extracted. Recovery of corn oil from thin stillage can be achieved by extraction systems and methods known in the art, including evaporation, centrifugation, and solvent extraction. In a specific embodiment, the second thin stillage provides an additional yield of DCO of from about 0.1 to 0.5 lbs per bushel of corn feedstock. In another specific embodiment, the additional yield of DCO is from about 0.1 lbs to about 0.7 lbs per pound of wet cake solids.

Figure 10:
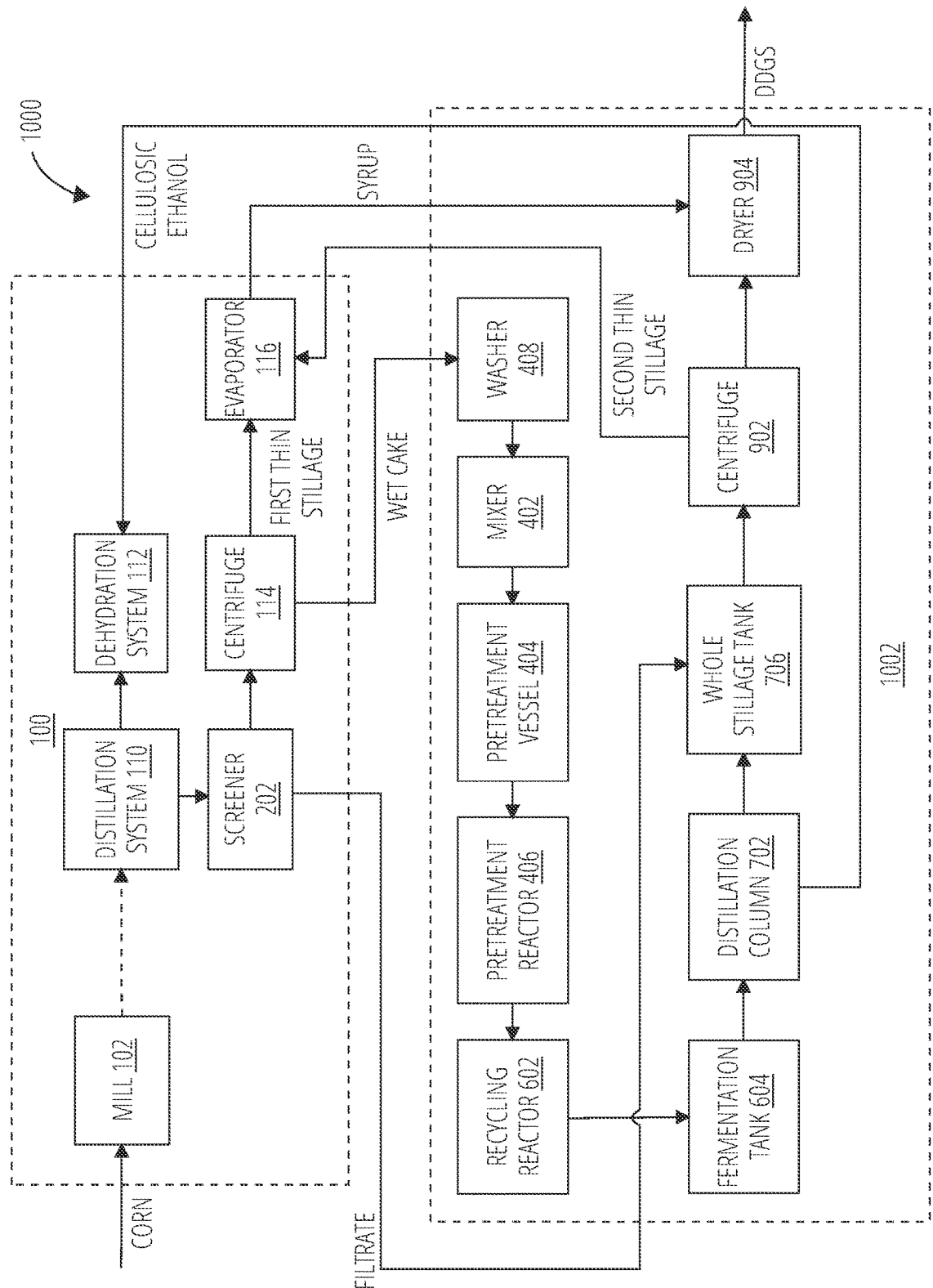
FIG. 10 illustrates an enhanced ethanol production plant and associated methods in accordance with particular embodiments.

It is contemplated that particular benefits may arise from adding one or more of the processes described above to an existing corn-based ethanol production process. In one aspect, this can provide additional ethanol production in the form of a cellulosic ethanol stream. As illustrated in FIG. 10 (a portion of which is shown in FIG. 1) which shows an enhanced ethanol production plant 1000 in accordance with the present disclosure, a method for increasing ethanol production associated with an existing ethanol production plant 100 can comprise feeding wet cake resulting from separation of first whole stillage into a cellulosic ethanol production process 1002, which can comprise any of the steps and processes described above. As illustrated in FIG. 10, equipment for this added process can comprise, without limitation, a washer 408 for the step of washing the wet cake; a mixer 402 for the step of acidification by mixing acid into the wet cake; a pretreatment vessel 404 for the step of agitating the acidified wet cake; a pretreatment reactor 406 for performing the second pretreatment stage; a recycling reactor 602 in which the wet cake is recycled with enzymes to initiate enzymatic hydrolysis; a fermentation tank 604 for furthering the hydrolysis of the wet cake and fermenting sugars produced in the foregoing processes; and a distillation column 702 to recover a stream of cellulosic ethanol and produce a by-product of second whole stillage. In a particular example as shown in FIG. 10, the cellulosic ethanol stream can be directed to an existing dehydration system 112 system in the existing ethanol production plant 100. In another particular example as shown in FIG. 10, first whole stillage from the distillation system 110 can be filtered in a screener 202 and the resulting filtrate combined with second whole stillage in a whole stillage tank 706, wherein protein contained in the filtrate bypasses the intervening stages.

In another aspect, a modification of existing corn-based ethanol production provides an increased yield of distillers corn oil. As illustrated in FIG. 10, a method for increasing distillers corn oil production associated with an existing ethanol production plant 100 is also provided by feeding wet cake resulting from centrifuge 114 of first whole stillage into a cellulosic ethanol production process 1002. The second whole stillage by-product from the distillation column 702 is separated with a centrifuge 902 into a low-fiber slurry and second thin stillage. In a particular embodiment as shown in FIG. 10, the second thin stillage is combined with the first thin stillage for evaporation to produce a syrup from which distillers corn oil is extracted. The syrup from the existing ethanol plant's evaporator and the low-fiber slurry can then be directed to a dryer 904 for preparation of a DDGS in accordance with the present disclosure. The dryer 904 may be dedicated to drying of the low-fiber slurry and syrup, due to all of the wet cake from the existing ethanol production plant being directed to the added cellulosic ethanol production.

Figure 11:
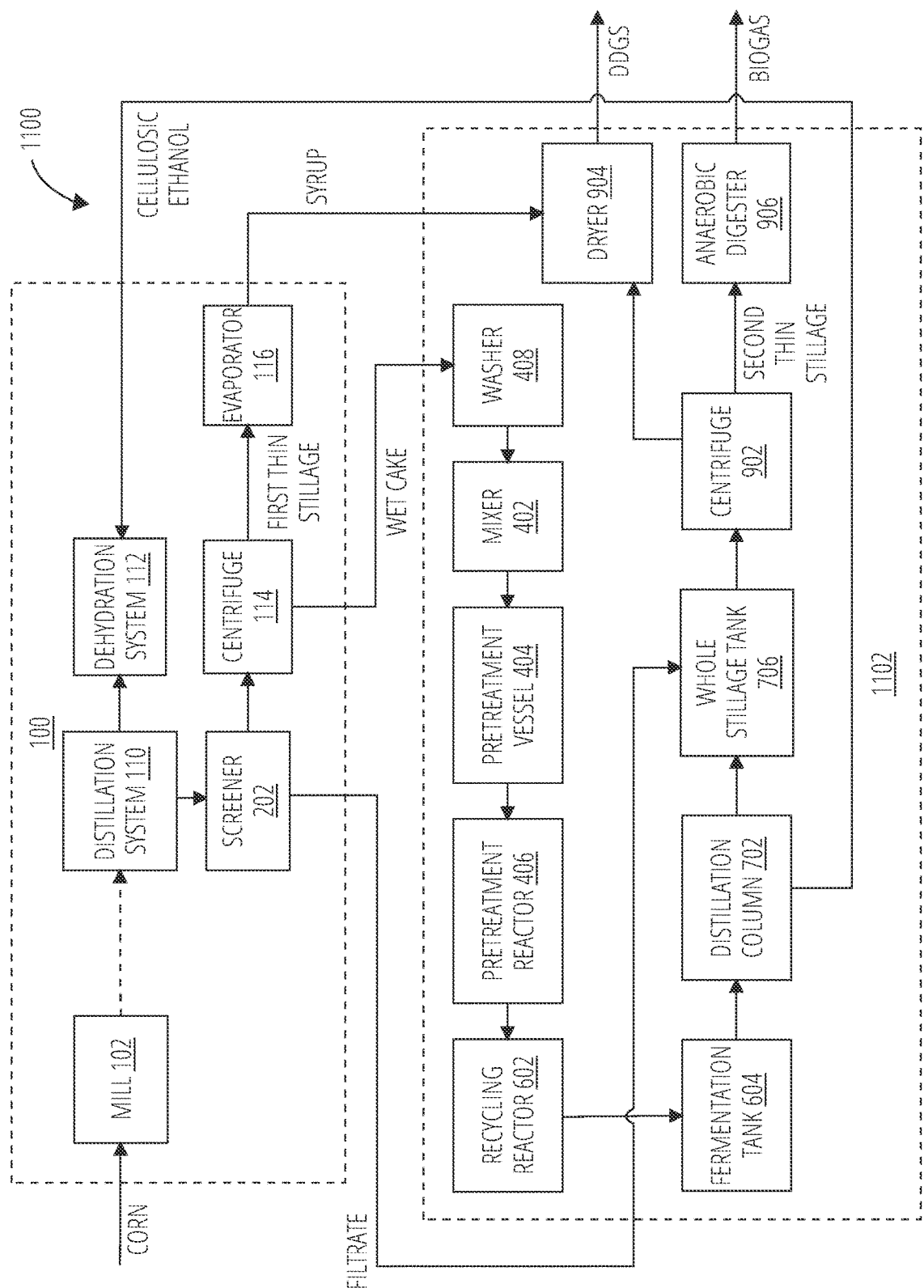
FIG. 11 illustrates an enhanced ethanol production plant and associated methods in accordance with particular embodiments.

In an alternative embodiment of an enhanced ethanol production plant 1100 as shown in FIG. 11, the second thin stillage can be directed to an anaerobic digester 906, where anaerobic digestion can be performed on the second thin stillage to produce a biogas which can be scrubbed and added to existing natural gas pipelines or the biogas can be used in the primary ethanol plant's boiler. This approach may be undertaken as an effective way to remove the chemical oxygen demand of the second thin stillage.

It will be appreciated from the foregoing that energy expenditures and costs associated with the added processes can be offset to a degree, not only by the added value of increased product and co-product streams, but also by directing process outputs back into appropriate units of the existing plant. In addition, resources and by-products associated with individual processes can be re-used or re-purposed. For example, steam generated from flashing steps can be used for heating in other steps such as acidification and pretreatment, as well as for driving beer through distillation columns. In addition, the enhanced production provided by the processes described herein allow existing ethanol production plants to forego resource-intensive corn milling techniques (e.g., wet milling) in preparing the corn feedstock for use.

EXAMPLE EMBODIMENTS

Example 1

Corn wet cake from primary ethanol production was subjected to the following cellulosic ethanol production process to produce a dried distillers grains with solubles. Steps 1-5 were performed at an ethanol plant modified according to embodiments herein. Steps 6-9 were performed at a research center according to embodiments herein.

1. The corn wet cake (3,473 lbs, 32% solids) was mixed in an agitated cone bottom tank with 135 gallons of process condensate (water) and 85 lbs of 40 wt % sulfuric acid;
2. The acidified wet cake was heated with direct steam injection to about 190° F. and held at that temperature for one hour (i.e., first pretreatment);
3. The wet cake was pumped through a horizontal plug flow reactor at about 280° F. with a residence time of 25 minutes (i.e., second pretreatment);
4. Wet cake was continuously discharged from the reactor to the flash tank and then to the enzymatic hydrolysis tank. The temperature of the wet cake was lowered to 140° F. and the pH was adjusted to 4.5 with aqueous ammonia, and cellulase and hemicellulase enzymes were added;
5. Hydrolysis proceeded for about 50 hours; the temperature was lowered to 95° F. followed by addition of a GMO *Saccharomyces* yeast and fermentation for about 50 hours;
6. The resulting beer was distilled in a beer column;
7. The whole stillage was decanted in a centrifuge to produce a second wet cake and thin stillage (i.e., second thin stillage);
8. The thin stillage was evaporated to produce syrup;
9. The syrup was combined with the second wet cake and dried in a ring dryer to produce DDGS having the following properties:

TABLE 1

Chemical and Physical properties of typical dried distillers grains with solubles (DDGS) produced from the cellulosic ethanol process described above. The DDGS exhibited a typical density of 35-37 lbs/ft$^3$.

Chemical and Physical Properties

|  | Min | Max |
| --- | --- | --- |
| Moisture % | — | 13.0 |
| Total Protein, % | 40.0 | — |
| Fiber (crude), % | — | 2.0 |
| Fat (crude), % | 1 | — |
| Ash, % |  | 8.0 |

TABLE 2

Energy analysis of the dried distillers grains with solubles.

| Energy | Typical, d.b. | |
| --- | --- | --- |
|  | Kcal/lb | kcal/kg |
| Digestible Energy | 1600 | 3530 |
| Metabolizable Energy | 1100 | 2425 |
| Net Energy Gain | 600 | 1320 |
| Net Energy Maintenance | 900 | 1985 |
| Net Energy Lactation | 800 | 1765 |
| Total Digestible Nutrients, % | 88 |  |

TABLE 3

Nutritional content of the dried distillers grains with solubles

|  | Typical, % DM |
| --- | --- |
| Nutrients |  |
| Protein | 45 |
| Fat | 1.5 |
| Fiber | 1.5 |
| ADF | 3.5 |
| NDF | 4 |
| Ash | 8 |
| Alanine | 3.6 |
| Arginine | 1.5 |
| Aspartic Aid | 2.8 |
| Cystine | 0.8 |
| Glutamic Acid | 8.9 |
| Glycine | 1.7 |
| Histidine | 1 |
| Isoleucine | 1.7 |
| Leucine | 5.6 |
| Lysine | 1 |
| Methionine | 1 |
| Phenylalanine | 2.3 |
| Proline | 3.9 |
| Serine | 2.4 |
| Threonine | 1.7 |
| Tryptophan | 0.3 |
| Tyrosine | 1.7 |
| Valine | 2.2 |
| Vitamins |  |
| Vitamin A, IU/100 g | 107.2 |
| Vitamin E IU/kg | 535 |

TABLE 3-continued

Nutritional content of the dried distillers grains with solubles

| | |
|---|---|
| Niacin mg/kg | 19.6 |
| Inositol mg/100 G | 2020 |
| Folic Acid mg/kg | 0.89 |
| Protein-Ruminants | |
| Estimated RUP, % CP | 69 |
| Rumen, % CP | 41 |
| Intestine, % CP | 42 |
| Total digested, % CP | 74 |

| | Typical, as is |
|---|---|
| Minerals | |
| Magnesium, % | 0.5 |
| Phosphorus, % | 1.7 |
| Potassium, % | 1.7 |
| Chloride, % | 0.2 |
| Sulfur, % | 1.7 |

TABLE 3-continued

Nutritional content of the dried distillers grains with solubles

| | |
|---|---|
| Calcium, ppm | 300 |
| Sodium, ppm | 400 |
| Copper, ppm | 8.6 |
| Iron, ppm | 795 |
| Manganese, ppm | 25 |
| Selenium, ppm | 0.2 |
| Zinc, ppm | 79 |

Example 2

The effect of three parameters (% acid added, temperature, and residence time) were measured in forty-three trials in which corn wet cake was subjected to a two-stage pretreatment process similar to Steps 1-2 (first pretreatment stage) and Step 3 (second pretreatment stage) in Example 1. The yields of soluble sugars and monomeric sugars resulting from each stage are shown below.

TABLE 4

Percent yields of five soluble sugars produced in the first pretreatment stage.

| First Pretreatment Stage | % Acid Added | Temp (° F.) | Time (min) | Yield of Total Soluble Sugars | | | | |
|---|---|---|---|---|---|---|---|---|
| | | | | Glucose | Xylose | Galactose | Arabinose | Mannose |
| Average | 3.7 | 188 | 64 | 39.0% | 96.8% | 94.7% | 98.4% | 83.4% |
| MIN | 2.0 | 162 | 10 | 19.3% | 87.3% | 64.6% | 91.2% | 0.0% |
| MAX | 6.2 | 196 | 307 | 51.3% | 100.0% | 100.0% | 100.0% | 100.0% |
| Std Dev | 0.9 | 8.6 | 67 | 6.2% | 3.5% | 8.2% | 2.4% | 22.6% |

TABLE 5

Percent yields of five monomeric sugars produced in the first pretreatment stage.

| First Pretreatment Stage | % Acid Added | Temp (° F.) | Time (min) | Yield of Monomeric Sugars | | | | |
|---|---|---|---|---|---|---|---|---|
| | | | | Glucose | Xylose | Galactose | Arabinose | Mannose |
| Average | 3.7 | 188 | 64 | 1.7% | 7.1% | 11.6% | 52.0% | 16.1% |
| MIN | 2.0 | 162 | 10 | 0.0% | 0.7% | 3.0% | 2.3% | 0.0% |
| MAX | 6.2 | 196 | 307 | 7.9% | 20.4% | 42.1% | 89.8% | 69.4% |
| Std Dev | 0.9 | 8.6 | 67 | 2.3% | 4.4% | 7.9% | 16.1% | 17.1% |

TABLE 6

Percent yields of five soluble sugars produced in the second pretreatment stage.

| Second Pretreatment Stage | % Acid Added | Temp (° F.) | Time (min) | Yield of Total Soluble Sugars | | | | |
|---|---|---|---|---|---|---|---|---|
| | | | | Glucose | Xylose | Galactose | Arabinose | Mannose |
| Average | 3.8 | 268 | 32 | 41.2% | 92.8% | 91.6% | 90.9% | 81.0% |
| MIN | 2.0 | 244 | 3 | 16.4% | 54.0% | 63.5% | 46.2% | 0.0% |
| MAX | 6.2 | 320 | 205 | 52.4% | 100.0% | 100.0% | 100.0% | 100.0% |
| Std Dev | 1.0 | 15 | 28 | 6.1% | 7.7% | 10.1% | 8.8% | 21.1% |

TABLE 7

Percent yields of five monomeric sugars produced in the second pretreatment stage.

| Second Pretreatment Stage | % Acid Added | Temp (° F.) | Time (min) | Yield of Monomeric Sugars | | | | |
|---|---|---|---|---|---|---|---|---|
| | | | | Glucose | Xylose | Galactose | Arabinose | Mannose |
| Average | 3.8 | 268 | 32 | 7.6% | 25.3% | 40.6% | 70.4% | 23.4% |
| MIN | 2.0 | 244 | 3 | 0.0% | 2.8% | 5.6% | 22.1% | 0.0% |
| MAX | 6.2 | 320 | 205 | 20.4% | 60.0% | 99.3% | 96.4% | 119.8% |
| Std Dev | 1.0 | 15 | 28 | 5.5% | 13.8% | 20.3% | 10.8% | 26.8% |

The above yields were determined by liquid chromatography. It is believed that the results reported for mannose, particularly the minimum percent yields ("MIN"), may reflect interference from other compounds in the samples.

While specific embodiments and applications have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

What is claimed is:

1. A method for hydrolyzing lignocellulosic material, comprising:
    flashing a lignocellulosic material in a flash drum to generate vapor;
    feeding the lignocellulosic material into a recycling reactor at a feed rate;
    adding at least one enzyme to the lignocellulosic material; and
    recycling the lignocellulosic material and at least one enzyme through the recycling reactor at a recycle rate and a residence time to hydrolyze the lignocellulosic material to produce an amount of monomeric sugar in the lignocellulosic material,
    wherein recycling comprises at least a portion of the lignocellulosic material and at least one enzyme exiting the recycling reactor and being recirculated back into the recycling reactor, and
    wherein recycling the lignocellulosic material and the at least one enzyme reduces a viscosity of fresh lignocellulosic material entering the recycling reactor, and
    wherein partially saccharified lignocellulosic material exiting the recycling reactor has a viscosity of 250 centipoise (cp) to 3000 cp.

2. The method of claim 1, further comprising directing the lignocellulosic material and at least one enzyme to a fermenter and fermenting the monomeric sugar using a microbe.

3. The method of claim 1, further comprising adding a base to the lignocellulosic material prior to adding the at least one enzyme.

4. The method of claim 3, wherein the at least one base is selected from at least one of ammonia, aqua ammonia, sodium hydroxide, sodium bicarbonate, potassium hydroxide, potassium carbonate, calcium hydroxide, or magnesium hydroxide.

5. The method of claim 1, further comprising cooling the lignocellulosic material to a target temperature for enzymatic activity of the at least one enzyme.

6. The method of claim 1, wherein the recycle rate is from about 1 to about 10 times the feed rate.

7. The method of claim 1, wherein the recycle rate is from about 5 to about 10 times the feed rate.

8. The method of claim 1, wherein the residence time is from about 6 hours to about 15 hours.

9. The method of claim 1, wherein the at least one enzyme is selected from a cellulase, a hemicellulase, or both.

10. The method of claim 1, wherein the at least one enzyme is selected from the group consisting of cellulase, xylanase, arabinase, galactidase, mannase, amylase, and beta-glucosidase.

11. A system for saccharification of lignocellulosic material, comprising:
    a flash drum configured to flash a vapor off the lignocellulosic material;
    a recycling reactor configured to: receive the lignocellulosic material from the flash drum at a feed rate; receive at least one enzyme; and to react the lignocellulosic material with the at least one enzyme; and
    a recycle stream configured to circulate at least a portion of the reacted lignocellulosic material and at least one enzyme exiting the recycling reactor back into the recycling reactor at a recycle rate that is greater than the feed rate,
    wherein recycling the lignocellulosic material and the at least one enzyme reduces a viscosity of fresh lignocellulosic material entering the recycling reactor, and
    wherein partially saccharified lignocellulosic material exiting the recycling reactor has a viscosity of 250 centipoise (cp) to 3000 cp.

12. The system for saccharification of claim 11, wherein the recycle rate is from about 1 to about 10 times the feed rate.

13. The system for saccharification of claim 11, further comprising a pump operably connected to the recycling reactor.

14. The system for saccharification of claim 11, wherein the recycling reactor is further configured to receive a base.

15. The method of claim 1, wherein the at least one enzyme is mixed substantially uniformly throughout the lignocellulosic material during the residence time.

16. The system for saccharification of claim 11, wherein the recycling reactor and the recycle stream are configured to mix the at least one enzyme substantially uniformly throughout the lignocellulosic material.

* * * * *